United States Patent [19]

Molde

[11] 4,433,026

[45] Feb. 21, 1984

[54] CLOTH-LIKE MATERIAL FOR FORMING A SURGICAL GOWN AND/OR A SURGICAL DRAPE AND METHOD OF MAKING THE SAME

[75] Inventor: Bradley J. Molde, Pleasant Plains, Ohio

[73] Assignee: Standard Textile Company, Inc., Cincinnati, Ohio

[21] Appl. No.: 316,080

[22] Filed: Oct. 29, 1981

[51] Int. Cl.$^3$ .............................................. B32B 7/00
[52] U.S. Cl. .................................. 428/252; 428/253; 428/315.5; 428/315.9
[58] Field of Search ............... 428/252, 253, 421, 422, 428/480, 315.5, 315.9

[56] References Cited

U.S. PATENT DOCUMENTS 4,233,358 11/1980 Jones .................................. 428/253

Primary Examiner—Marion McCamish
Attorney, Agent, or Firm—Kinney and Schenk

[57] ABSTRACT

A cloth-like material for forming a surgical gown and/or a surgical drape, the material comprising a three-layer flexible laminate having a middle layer of plastic film material and two outer layers of plastic fabric material secured to opposed sides of the middle layer. The middle layer is substantially water proof and air breathable. One of the outer layers is substantially dimensionally stable. The other of the outer layers is substantially dimensionally unstable so as to generally conform to the stable outer layer.

18 Claims, 2 Drawing Figures

CLOTH-LIKE MATERIAL FOR FORMING A SURGICAL GOWN AND/OR A SURGICAL DRAPE AND METHOD OF MAKING THE SAME

BACKGROUND OF THE INVENTION

1. Field of the Invention

This invention relates to an improved cloth-like material for forming a surgical gown and/or a surgical drape and to a method of making the same, as well as to an improved surgical drape and method of making the same.

2. Prior Art Statement

It is known to provide a cloth-like material for forming a surgical gown and/or a surgical drape wherein the material is disposable after one use or the material can be reusable through laundering thereof.

It is believed that all of the prior known materials have a linting problem.

SUMMARY OF THE INVENTION

It is one feature of this invention to provide an improved cloth-like material for forming a surgical gown and/or a surgical drape that has improved characteristics over prior known cloth-like materials utilized for forming surgical gowns and/or surgical drapes.

In particular, it was found according to the teachings of this invention that the prior known cloth-like materials for forming surgical gowns and/or surgical drapes, whether disposable or reusable, all had a linting problem wherein lint from the material could fall into an open wound or incision of the patient and later cause a post-operative infection or like.

In addition, it was found according to the teachings of this invention that the prior known cloth-like materials that are reusable do not permit a large number of reuse cycles thereof because the same wear out through the repeated laundering operations.

Also, it was found according to the teachings of this invention that it would be desirable to improve upon the waterproofness of the reusable cloth-like materials utilized for forming a surgical gown and/or a surgical drape in order to improve the prevention of bacteria migration through such material.

However, it was also realized that it is also desirable to provide a material that breathes not only for the purpose of permitting the material to be steam autoclaved for recycling the material, but also to make the patient and/or other user of the drape or gown more comfortable.

In addition, it was realized that it is desirable to have a light weight material as well as a material that readily drapes.

Accordingly, it was found according to the teachings of this invention that a three-layer flexible laminate could be provided which would perform all of the above functions and have all of the above desired features.

For example, one embodiment of this invention provides a cloth-like material for forming a surgical gown and/or a surgical drape, the material comprising a three layer flexible laminate having a middle layer of plastic film material and two outer layers of plastic fabric material secured to opposed sides of the middle layer. The middle layer is substantially waterproof and air breathable. One of the outer layers is substantially dimensionally stable. The other of the outer layers is substantially dimensionally unstable so as to generally conform to the stable outer layer. In other words, one of the outer layers is relatively non-stretchable while the other of the outer layers is relatively stretchable in at least one dimension.

Accordingly, it is an object of this invention to provide an improved cloth-like material for forming a surgical gown and/or a surgical drape, the cloth-like material of this invention having one or more of the novel features of this invention as set forth above or hereinafter shown or described.

Another object of this invention is to provide an improved method of making such a cloth-like material, the method of this invention having one or more of the novel features of this invention as set forth above or hereinafter shown or described.

Another object of this invention is to provide an improved surgical drape having one or more of the novel features of this invention as set forth above or hereinafter shown or described.

Another object of this invention is to provide a method of making such an improved surgical drape, the method of this invention having one or more of the novel features of this invention as set forth above or hereinafter shown or described.

Other objects, uses and advantages of this invention are apparent from a reading of this description which proceeds with reference to the accompanying drawings forming a part thereof and wherein:

DESCRIPTION OF THE PREFERRED EMBODIMENTS

Figure 1:
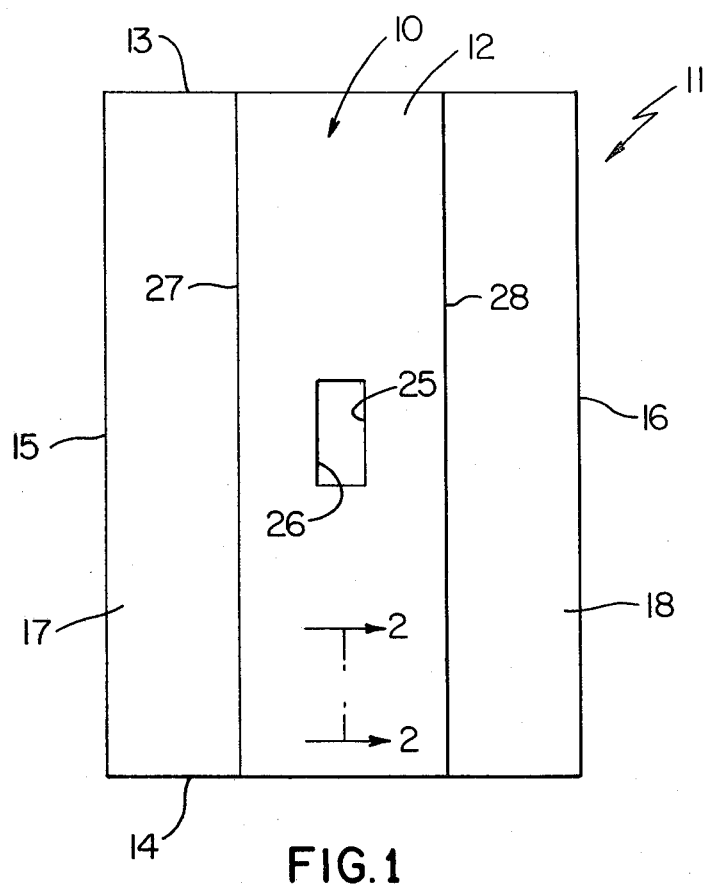
FIG. 1 is a plan view of one embodiment of the improved surgical drape of this invention.

While the various features of this invention are hereinafter described and illustrated as being particularly adapted to provide a cloth-like material for forming a surgical gown and/or a surgical drape, it is to be understood that the cloth-like material of this invention can be utilized for other purposes as desired.

Therefore, this invention is not to be limited to only the embodiments illustrated in the drawings, because the drawings are merely utilized to illustrate one of the wide variety of uses of this invention.

Figure 2:
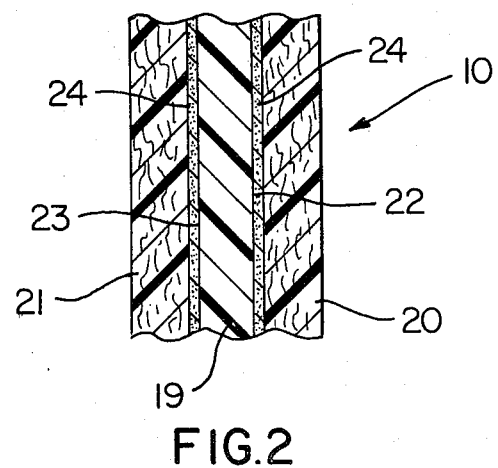
FIG. 2 is an enlarged fragmentary cross-sectional view taken on line 2—2 of FIG. 1 and not only shows the cloth-like material of this invention for forming the surgical drape of FIG. 1, but also shows the cloth-like material of this invention utilized for forming surgical gowns and/or other surgical drapes.

Referring now to FIGS. 1 and 2, the improved cloth-like material of this invention is generally indicated by the reference numeral 10 and is illustrated in FIG. 1 as forming an improved surgical drape of this invention that is generally indicated by the reference numeral 11 and is formed in a substantially rectangular configuration in which a central section 12 thereof and extending between the opposed ends 13 and 14 thereof is formed completely of the improved cloth-like material 10 of this invention.

The drape 11 has opposed end edges 15 and 16 defined by side extensions 17 and 18 of the central section 12, the extensions 17 and 18 respectively comprising one layer of the cloth-like material of this invention as will be apparent hereinafter.

As illustrated in FIG. 2 the improved cloth-like material 10 of this invention comprises a three-layer flexible laminate having a middle layer 19 of plastic film material and two outer layers 20 and 21 of plastic fabric material secured to opposed sides 22 and 23 of the middle layer 19 by suitable adhesive means 24 spot coated or the like on the opposed sides 22 and 23 of the middle layer 19. As used herein, the term "plastic" identifies a capability of permanently changing shape in any direction without breaking apart and indicates such fabrics as polyester.

The middle layer 19 is substantially waterproof and air breathable while the outer layer 20 is substantially dimensionally stable and the other outer layer 21 is substantially dimensionally unstable so as to generally conform to the stable layer 20.

In this manner, it was found that the outer unstable layer 21 protects the side 23 of the middle layer 19 during a steam autoclaving of the material 10 to render the same bacterial free after each use cycle thereof and by having the layer 21 unstable, the layer 21 will conform or mold to the contour and drape of the stable layer 20 which also functions to protect the side 22 of the middle layer 19 during the aforementioned steam autoclaving operation or other laundering operations, as desired.

It was found according to the teachings of this invention that both the stable layer 20 and unstable layer 21 could be formed from 100% polyester continuous filament yarn so that the material 10 will be substantially lint-free and by having the layer 20 woven in a poplin or regular broadcloth weave, the layer 20 would be substantially dimensionally stable. In contrast, it was found that if the layer 21 was formed of a knit it would be substantially dimensionally unstable to conform to the contour of the stable layer 20. Accordingly, it was found that the layer 21 can be a tri-cot knit.

The middle layer 19 comprises an expanded polytetrafluoroethylene film that is substantially microporous so as to be substantially waterproof and still air breathable. One such expanded polytetrafluoroethylene film is known under the trademark or tradename Gore-Tex manufactured by the W. L. Gore Associates, Inc., of Newark, Del.

While a specific example of a laminate 10 of this invention is hereinafter set forth as to the particular materials of the layers 19, 20 and 21 thereof, it is to be understood that this invention is not to be limited to such specific example because the layers 19, 20 and 21 can be formed from other materials that have the same characteristics and can be of other weights and thicknesses as desired because it is believed that one of the important features of this invention is to provide a middle layer of the three-layer laminate that is substantially waterproof and yet air breathable and to laminate on one side thereof a substantially stable plastic fabric material and on the other side thereof a substantially unstable plastic fabric material so as to conform to the stable layer thereof, the outer layers thereby protecting the middle layer.

Referring again to FIG. 1, the surgical drape 11 of this invention is a substantially large surgical drape so that it is not required that the cloth-like material 10 of this invention cover the entire area of use thereof. Thus, the extensions 17 and 18 can comprise a continuation of the outer layer 20 of the cloth-like material 10.

A substantially rectangular opening 25 is cut centrally through the central section 12 of the drape 11 for operation purposes, the opening 25 defining a substantially rectangular edge 26 of the material 10.

It is found that it is desirable to hem, embroider or whip stitch not only the edge 26 of the opening 25 in the section 12 of the drape 11, but also to hem, embroider or whip stitch the exposed edges 13, 14, 15 and 16 of the drape 11 in order to prevent delamination thereof during use thereof. Likewise, the edges 27 and 28 between the central section 12 of the drape 11 and the extensions 17 and 18 thereof could be embroidered or whip stitched in order to prevent delamination of the central section 12.

Of course, it is to be understood that the entire drape 11 could be formed of the material 10 of this invention without having the side extensions 17 and 18 thereon, if desired.

As previously stated, it has been found according to the teachings of this invention that the material 10 of this invention not only is substantially light-weight, drapable and waterproof so as to prevent bacteria migration therethrough, but also the material 10 of this invention readily lets steam pass through the same so that the material 10 can be readily steam autoclaved without resulting in delamination thereof and thereby permitting the material 10 to have many cycles of reuse thereof, such as being recycled up to 75 times or more.

Accordingly, it can be seen that this invention not only provides an improved cloth-like material for forming surgical gowns and/or surgical drapes, but also this invention provides a method of making such a cloth-like material.

As previously stated, this invention is not to be limited to a particular lamination of materials. However, one embodiment of such a cloth-like material 10 of this invention that has been found satisfactory is as follows.

The stable layer 20 comprises a sheet of nonlinting poplin material purchased from Milliken & Company, Spartanburg, S.C. and having a thickness of 14.5 mils and a weight of 4.7 oz./sq. yd. The middle layer 19 comprises a sheet of teflon made by W. L. Gore & Associates, Elkton, Md. and having a thickness of 1.0 mil. The unstable layer 21 comprises a sheet of knited tricote material manufactured by Winkler Knits, Shillington, Pa. and having a thickness of 10.0 mils and a weight of 2.0 oz./sq. yd. The adhesive 24 comprises a polyester adhesive manufactured by W. L. Gore & Associates.

While the forms and methods of this invention now preferred have been illustrated and described as required by the Patent Statute, it is to be understood that other forms and methods can be utilized and still fall within the scope of the appended claims.

What is claimed is:

1. In a cloth-like material for forming a surgical gown and/or a surgical drape, the improvement wherein said material comprises a three-layer flexible laminate having a middle layer of plastic film material and two outer layers of plastic fabric material secured to opposed sides of said middle layer with adhesive means, said middle layer being substantially microporous and thereby being substantially waterproof and air breathable, one of said outer layers being a woven plastic fabric material and thereby being substantially dimensionally stable, the other of said outer layers being a knitted plastic fabric material and thereby being substantially dimensionally unstable so as to generally conform to said one outer layer.

2. A cloth-like material for forming a surgical gown and/or a surgical drape as set forth in claim 1 wherein said one outer layer comprises a weave of a polyester continuous filament yarn.

3. A cloth-like material for forming a surgical gown and/or a surgical drape as set forth in claim 2 wherein said weave comprises a poplin weave.

4. A cloth-like material for forming a surgical gown and/or a surgical drape as set forth in claim 1 wherein said other outer layer comprises a knit of a polyester continuous filament yarn.

5. A cloth-like material for forming a surgical gown and/or a surgical drape as set forth in claim 4 wherein said knit comprises a tri-cot knit.

6. A cloth-like material for forming a surgical gown and/or a surgical drape as set forth in claim 1 wherein said middle layer comprises an expanded polytetrafluoroethylene micro-porous film.

7. A cloth-like material as set forth in claim 1 wherein one section thereof comprises said three-layer flexible laminate and another section thereof is formed from an extension of only one of said layers.

8. A cloth-like material as set forth in claim 7 wherein said one layer that forms said extension comprises said one outer layer.

9. In a cloth-like material for forming a surgical gown and/or a surgical drape, the improvement wherein said material comprises a three-layer flexible laminate having a middle layer of plastic film material and two outer layers of plastic fabric material secured to opposed sides of said middle layer, said middle layer being substantially waterproof and air breathable, one of said outer layers being substantially dimensionally stable, the other of said outer layers being substantially dimensionally unstable so as to generally conform to said one outer layer, said outer layers being secured to said middle layer by adhesive means, said one outer layer comprising a poplin weave of a polyester continuous filament yarn, said other outer layer comprising a tri-cot knit of a polyester continuous filament yarn, said middle layer comprising an expanded polytetrafluoroethylene micro-porous film.

10. In a method of making a cloth-like material for forming a surgical gown and/or a surgical drape, the improvement comprising the steps of forming a three-layer flexible laminate having a middle layer of plastic film material and two outer layers of plastic fabric material secured to opposed sides of said middle layer with adhesive means, forming said middle layer to be substantially micro-porous and thereby be substantially waterproof and air breathable, forming one of said outer layers to be a woven plastic fabric material and thereby be substantially dimensionally stable, and forming the other of said outer layers to be a knitted plastic fabric material and thereby be substantially dimensionally unstable so as to generally conform to said one outer layer.

11. A method of making a cloth-like material for forming a surgical gown and/or a surgical drape as set forth in claim 10 and including the step of forming said one outer layer to comprise a weave of a polyester continuous filament yarn.

12. A method of making a cloth-like material for forming a surgical gown and/or a surgical drape as set forth in claim 11 and including the step of forming said weave to comprise a poplin weave.

13. A method of making a cloth-like material for forming a surgical gown and/or a surgical drape as set forth in claim 10 and including the step of forming said other outer layer to comprise a knit of a polyester continuous filament yarn.

14. A method of making a cloth-like material for forming a surgical gown and/or a surgical drape as set forth in claim 13 and including the step of forming said knit to comprise a tri-cot knit.

15. A method of making a cloth-like material for forming a surgical gown and/or a surgical drape as set forth in claim 10 and including the step of forming said middle layer to comprise an expanded polytetrafluoroethylene micro-porous film.

16. A method of making a cloth-like material as set forth in claim 11 and including the step of forming one section thereof to be formed of said three-layer flexible laminate and another section thereof to be formed from an extension of only one of said layers.

17. A method of making a cloth-like material as set forth in claim 16 and including the step of forming said one layer that forms said extension to comprise said one outer layer.

18. In a method of making a cloth-like material for forming a surgical gown and/or a surgical drape, the improvement comprising the steps of forming a three-layer flexible laminate having a middle layer of plastic film material and two outer layers of plastic fabric material secured to opposed sides of said middle layer, forming said middle layer to be substantially waterproof and air breathable, forming one of said outer layers to be substantially dimensionally stable, forming the other of said outer layers to be substantially dimensionally unstable so as to generally conform to said one outer layer, securing said outer layers to said middle layer with adhesive means, forming said one outer layer to comprise a poplin weave of a polyester continuous filament yarn, forming said other outer layer to comprise a tri-cot knit of a polyester continuous filament yarn, and forming said middle layer to comprise an expanded polytetrafluoroethylene micro-porous film.

* * * * *